US009220462B2

(12) United States Patent
Sethi

(10) Patent No.: US 9,220,462 B2
(45) Date of Patent: Dec. 29, 2015

(54) IMAGING SENSOR AND METHOD FOR BIOMETRIC MAPPING OF FACIAL SKIN

(71) Applicant: Toshiba America Electronic Components, Inc., San Jose, CA (US)

(72) Inventor: Rakesh Sethi, San Jose, CA (US)

(73) Assignee: Toshiba America Electronic Components, Inc., Irvine, CA (US)

( * ) Notice: Subject to any disclaimer, the term of this patent is extended or adjusted under 35 U.S.C. 154(b) by 172 days.

(21) Appl. No.: 13/902,541

(22) Filed: May 24, 2013

(65) Prior Publication Data

US 2014/0347512 A1 Nov. 27, 2014

(51) Int. Cl.
*A61B 5/00* (2006.01)
*A61B 5/103* (2006.01)
*H04N 5/232* (2006.01)

(52) U.S. Cl.
CPC .............. *A61B 5/6898* (2013.01); *A61B 5/0022* (2013.01); *A61B 5/1032* (2013.01); *A61B 5/441* (2013.01); *H04N 5/23219* (2013.01); *A61B 5/743* (2013.01); *A61B 2576/00* (2013.01); *Y10T 29/49826* (2015.01)

(58) Field of Classification Search
CPC .................... H04N 5/23229; H04N 5/23219
See application file for complete search history.

(56) References Cited

U.S. PATENT DOCUMENTS

| | | | |
|---|---|---|---|
| 5,237,452 A * | 8/1993 | Okayama et al. .............. 359/574 |
| 5,671,735 A | 9/1997 | Macfarlane et al. | |
| 6,128,516 A | 10/2000 | Macfarlane et al. | |
| 6,129,664 A | 10/2000 | Macfarlane et al. | |
| 6,208,749 B1 | 3/2001 | Gutkowicz-Krusin et al. | |
| 6,437,863 B1 | 8/2002 | Macfarlane et al. | |
| 7,233,693 B2 | 6/2007 | Momma | |
| 7,471,321 B2 * | 12/2008 | Ojima .................... H04N 9/045 348/272 |
| 7,657,101 B2 | 2/2010 | Christiansen, II et al. | |
| 7,773,143 B2 | 8/2010 | Feldman et al. | |
| 7,840,064 B2 * | 11/2010 | Chhibber ........... G06K 9/00288 382/115 |
| 7,865,076 B2 | 1/2011 | Tamaki et al. | |
| 8,155,413 B2 | 4/2012 | Chhibber et al. | |

(Continued)

OTHER PUBLICATIONS

Master Thesis Report, Kusse Sukuta Bersah entitled Spectral Imaging and Analysis of Human Skin dated Jun. 21, 2010.

(Continued)

*Primary Examiner* — Ahmed A Berhan
(74) *Attorney, Agent, or Firm* — Ulmer & Berne LLP

(57) ABSTRACT

A diagnostic system for biometric mapping of facial skin includes a light filter a light sensor, a non-transient memory, a correlation processor, and an output unit. The light filter filters light reflected from an object to a filtered light signal. The light sensor receives the filtered light signal and generates a first electronic image signal representative of an image of the object in accordance with the filtered light signal. The memory stores a first electronic diagnostic signal representative of a predetermined mal-condition of the object. The processor determines a correlation between the first electronic image signal and the first electronic diagnostic signal, generates a correlation signal representative of a strength of the correlation, determines a diagnosis of the associated object based on the correlation signal, and generates a diagnosis signal in accordance with the diagnosis. The output unit generates a diagnosis result signal in accordance with the diagnosis signal.

21 Claims, 12 Drawing Sheets

(56) References Cited

U.S. PATENT DOCUMENTS

| | | | | |
|---|---|---|---|---|
| 8,254,674 B2* | 8/2012 | Nanu | ................ | G06T 5/008 382/117 |
| 8,855,751 B2* | 10/2014 | Kruglick | ................ | 600/476 |
| 2003/0169346 A1* | 9/2003 | Ojima et al. | ................ | 348/207.99 |
| 2005/0225654 A1* | 10/2005 | Feldman et al. | ................ | 348/272 |
| 2010/0054592 A1* | 3/2010 | Nanu et al. | ................ | 382/167 |
| 2011/0013006 A1* | 1/2011 | Uzenbajakava | ................ | A61B 5/0059 348/77 |

OTHER PUBLICATIONS

Imaged-based skin color and texture analysis/synthesis by extracting hemoglobin and melanin information in the skin.

Multispectral color imaging for dermatology: application in inflammatory and immunologi diseases (To be published in IS&T/SID 13th Color Imaging Conference, Scottsdale, AZ).

Specialized Remote Patients' Diagnostic Tool for Treatment Optimization, S. Doddick, C. Druzgalski, Dept. of Electrical/Biomedical Engineering, Cal. State Unv. Long Beach, CA.

\* cited by examiner

|  | C1 | | C2 | | C3 | | C4 | | C5 | |
|---|---|---|---|---|---|---|---|---|---|---|
| R1 | S | P | S | P | S | P | S | P | S | P |
|  | R/P | P/B | R/P | P/B | R/P | P/B | R/P | P/B | R/P | P/B |
| R2 | S | P | S | P | S | P | S | P | S | P |
|  | R/P | P/B | R/P | P/B | R/P | P/B | R/P | P/B | R/P | P/B |
| R3 | S | P | S | P | S | P | S | P | S | P |
|  | R/P | P/B | R/P | P/B | R/P | P/B | R/P | P/B | R/P | P/B |
| R4 | S | P | S | P | S | P | S | P | S | P |
|  | R/P | P/B | R/P | P/B | R/P | P/B | R/P | P/B | R/P | P/B |

FIG. 8a

IMAGING SENSOR AND METHOD FOR BIOMETRIC MAPPING OF FACIAL SKIN

FIELD

The subject application is directed to imaging systems and methods for biometric mapping of skin features. The application is particularly related to imaging systems with micro-filter elements for early detection or diagnosis of skin and other diseases and/or conditions, and for assessment of changes in selected skin characteristics over time.

BACKGROUND

Filters are commonly used in cameras to provide an interface between the subject being imaged and the electronic imaging system of the camera. For example, color filters may be used in photography to compensate for differences between the dynamic range of the light sensors within the camera and the range of available light relative to the subject being photographed.

In some cameras, red (R), green (G), and blue (B) filters are used. Often, standard electronic photography cameras use a color filter array or matrix wherein the RGB filter elements are disposed adjacent to the electronic light sensors of the camera in a particular arrangement or pattern to obtain a better conversion of the light from the subject being imaged into light usable by the camera. For example, in order to obtain a more realistic image of subjects in ordinary sun-lit conditions, many cameras having RGB filters utilize more green filter matrix elements than red or blue. Essentially, in these systems, the green filter elements of the RGB color filter array are over represented.

Evidence of some diseases manifest in skin discolorations which can be found by trained professionals through examination of the facial skin. For example, a certain redness of the facial skin can be an early indication of an oxygen deficient condition or of other blood diseases or the like. A yellowness of the skin can be an early sign of liver dysfunction or of a jaundice condition. However, standard photography cameras are not trained for redness or yellowness imaging and, further, are not well suited for imaging the human skin in general.

Although it is desirable to obtain a live diagnosis from trained professionals during an office visit, some medical conditions present themselves through dues in the characteristics of the facial skin over time. Accordingly, a single office visit might not lead to any meaningful diagnosis. However, meaningful quantification of redness, yellowness, or other discolorations of the skin of a patient over the course of multiple office visits remains an unresolved challenge using existing electronic photographic equipment.

BRIEF DESCRIPTION OF THE DRAWINGS

FIGS. 8a and 8b are plan views of color filter arrangements in accordance with the example embodiments;

DETAILED DESCRIPTION

Figure 1:
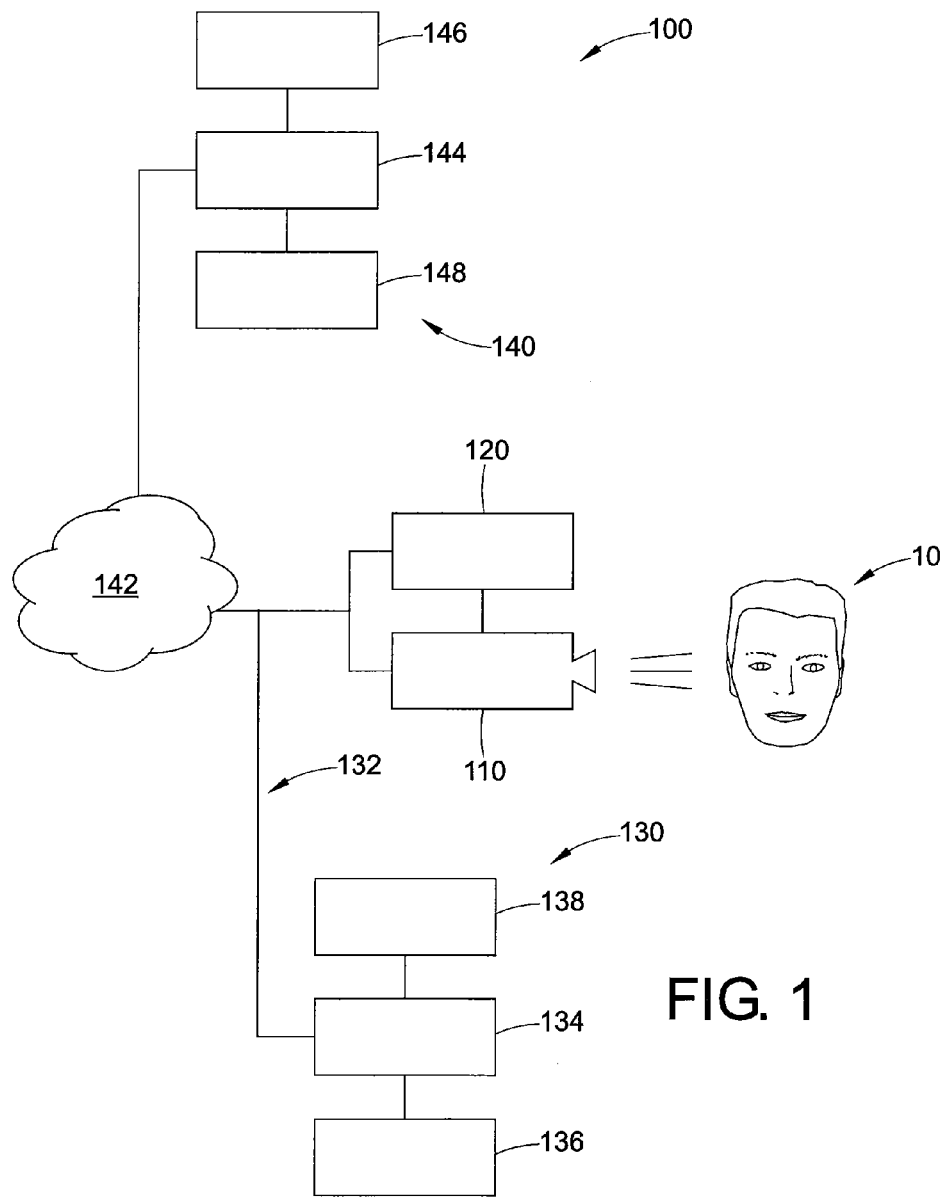
FIG. 1 is a simplified block diagram of a system for biometric mapping of the facial skin in accordance with an example embodiment.

With reference now to the drawings wherein the showings are for purposes of illustrating the example embodiments only, and not for purposes of limiting same, FIG. 1 is a block diagram of an image acquisition system 100 for performing a biometric mapping of the facial skin according to an example embodiment. The system 100 includes an image acquisition device 110 and at least one light source 120 operatively coupled with the image acquisition device 110. Although the image acquisition device of the example embodiment includes local processing capabilities as will be described in greater detail below, the device is operatively coupled with a first set 130 of local computational devices by a local area network (LAN) communication connection 132, and is further connected with a second set 140 of remote computational devices by a second communication network 142, wherein the second network is, in the example embodiment, the Internet. In one embodiment, the light source 120 generates polarized light. In another embodiment, the light source 120 generates infrared light. In a further embodiment, the light source 120 generates visible light.

In the example embodiment illustrated, the first set 130 of local computational devices includes a computing device 134, a memory 136 storing data and instructions for execution by the computing device 134, and an input/output device 138 for generating images such as on a display or hard copies of results obtained by the computing device 134. Similarly, the second set 140 of remote computational devices includes a computing device 144 operatively coupled with a memory 146 storing data and instructions executable by the computing device 144, and an input/output device 148 configured to generate images and/or hard copy outputs of results obtained by the computing device 144.

Figure 2:
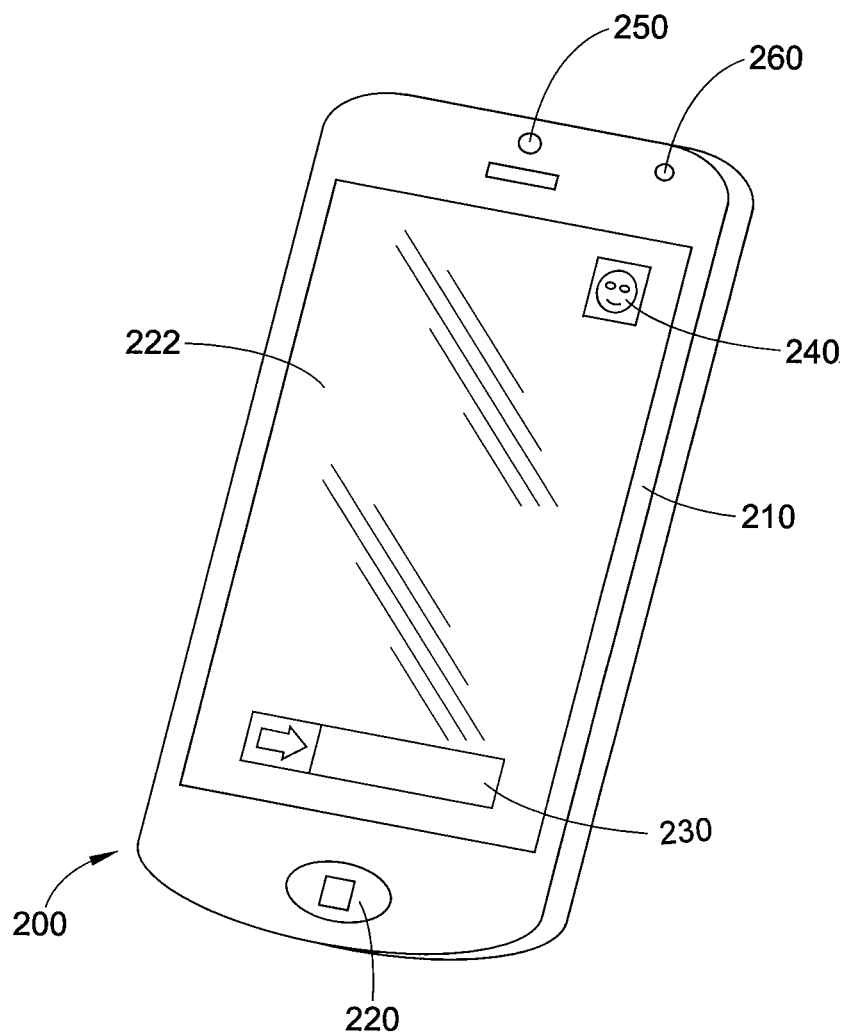
FIG. 2 is a line drawing showing an electronic image acquisition device in accordance with an example embodiment for use in the system of FIG. 2.

In an embodiment, as shown in FIG. 2, the image acquisition device 110 is integrated within a mobile communication device 200 such as, for example, a cellular phone 210, wherein, in the example embodiment, the cellular phone 210 is an iPhone™ device or any other equivalent Smart Phones now known or hereinafter developed. It is to be appreciated that the image acquisition device 110 may be integrated within portable or other photographic equipment or may be separately provided as a dedicated imaging system for biometric mapping of facial skin as well. The cellular phone 210 of the example embodiment illustrated includes a power switch 220, and a touch screen 222 for presenting data representative of functional commands to the user in a graphical format. For example, the touch screen is operable to present a slide bar icon 230 for unlocking the device so that it may be used by the end user, and data representative of a biometric imaging icon 240 operable by the user to select the biometric facial mapping capabilities and functionality of the device 200 by touching the icon shown on the screen 222.

In addition, the mobile communication device 200 includes a camera 250 and a light source 260, both being integrated into the body of the device. In the example, the camera 250 includes an image sensor (not shown) to be described in greater detail below for generating an electronic signal representative of an image, and an optical assembly (not shown) to be described in greater detail below adapted to direct light from outside of the mobile communication device 200 onto the image sensor. In one embodiment, the light source 260 generates polarized light. In another embodiment, the light source 260 generates infrared light. In a further embodiment, the light source 260 generates visible light.

Figure 3:
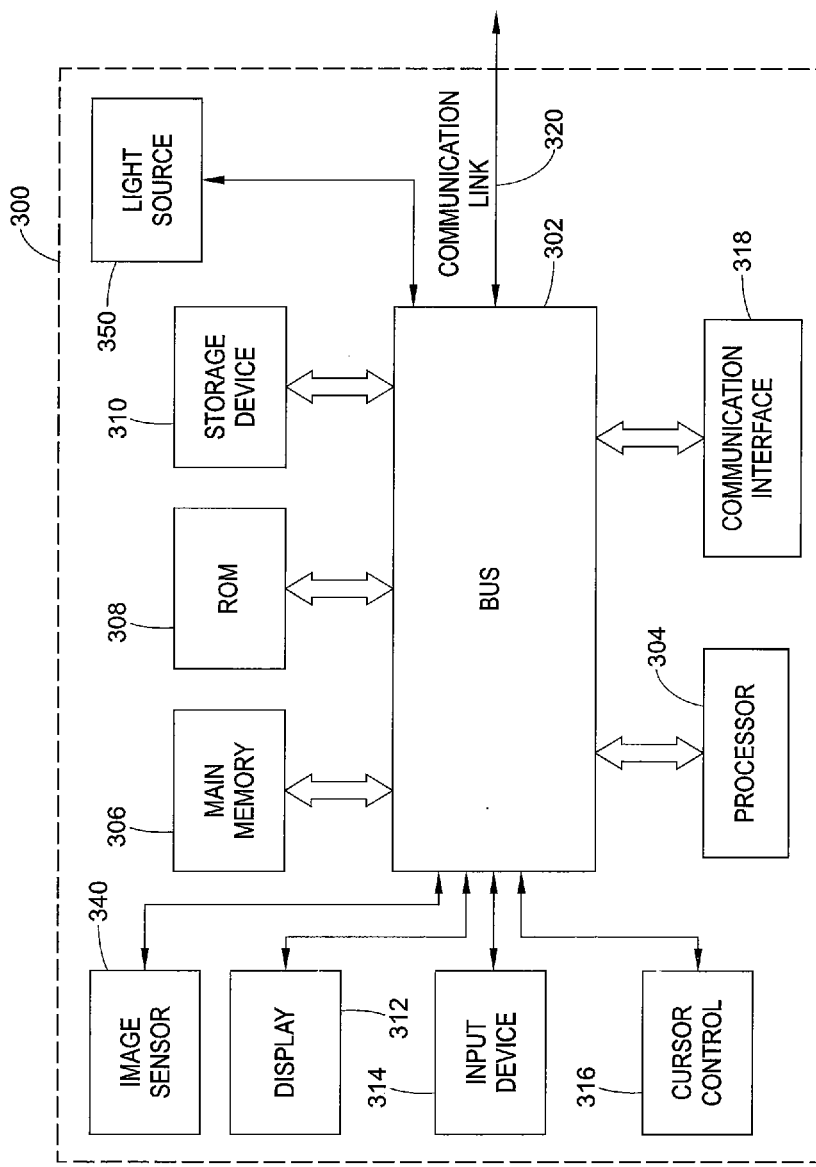
FIG. 3 is a functional block diagram illustration of a computer system upon which an example embodiment may be implemented.

FIG. 3 illustrates a computer system 300 upon which an example embodiment may be implemented. For example computer system 300 may be employed to implement the logic of the image acquisition device 110 (FIG. 1) and/or the mobile communication device 200 (FIG. 2). Computer system 300 may also be employed to implement the first set of local computational devices 130 and/or the second set of remote computational devices 140 together with or separate from the image acquisition device illustrated in FIG. 1.

Computer system 300 includes a bus 302 or other communication mechanism for communicating information and a processor 304 coupled with bus 302 for processing information. Computer system 300 also includes a main memory 306, such as random access memory (RAM) or other dynamic storage device coupled to bus 302 for storing information and instructions to be executed by processor 304. Main memory 306 also may be used for storing a temporary variable or other intermediate information during execution of instructions to be executed by processor 304. Computer system 300 further includes a read only memory (ROM) 308 or other static storage device coupled to bus 302 for storing static information and instructions for processor 304. A storage device 310, such as a magnetic disk or optical disk, is provided and coupled to bus 302 for storing information and instructions.

Computer system 300 may be coupled via bus 302 to a display 312 such as a cathode ray tube (CRT), liquid crystal display (LCD) or a touch screen 222 (FIG. 2), for displaying information to a computer system user. An input device 314, such as an auxiliary keyboard (not shown) including alphanumeric and other keys, and preferably the touch screen 222, is coupled to bus 302 for communicating information and command selections to processor 304. Another type of user input device is cursor control 316, such as by a mouse, a trackball, cursor direction keys or finger touch position for communicating direction information and command selections to processor 304 and for controlling cursor movement on display 312. This input device typically has two degrees of freedom in two axes, a first axis (e.g. x) and a second axis (e.g. y) that allows the device to specify positions in a plane. Input device 314 may be employed for manually entering keying data.

An aspect of the example embodiment is related to the use of computer system 300 for collecting one or more electronic images of a subject and performing biometric mapping of the images for early determination of disease or other trends in the facial skin of the subject. According to an example embodiment, imaging, biometric mapping, and other functions are provided by computer system 300 in response to processor 304 executing one or more sequences of one or more instructions contained in main memory 306. Such instructions may be read into main memory 306 from another computer-readable medium, such as storage device 310. Execution of the sequence of instructions contained in main memory 306 causes processor 304 to perform the process steps described herein. One or more processors in a multi-processing arrangement may also be employed to execute the sequences of instructions contained in main memory 306. In alternative embodiments, hard-wired circuitry may be used in place of or in combination with software instructions to implement an example embodiment. Thus, embodiments described herein are not limited to any specific combination of hardware circuitry and software.

The term "computer-readable medium" as used herein refers to any non-transitory medium that participates in providing instructions to processor 304 for execution. Such a medium may take many forms, including but not limited to non-volatile media and volatile media. Non-volatile media include for example optical or magnetic disks, such as storage device 310. Volatile media include dynamic memory such as main memory 306. Common forms of computer-readable media include for example floppy disk, a flexible disk, hard disk, magnetic cards, paper tape, any other physical medium with patterns of holes, a RAM, a PROM, an EPROM, a FLASHPROM, CD, DVD or any other memory chip or cartridge, or any other media from which a computer can read. "Logic," as used herein, includes but is not limited to hardware, firmware, software and/or combinations of each to perform a function(s) or an action(s), and/or to cause a function or action from another component. For example, based on a desired application or need, logic may include a software controlled microprocessor, discrete logic such as an application specific integrated circuit (ASIC), a programmable/programmed logic device, memory device containing instructions, or the like, or combinational logic embodied in hardware. Logic may also be fully embodied as software.

The computer system 300 further includes a light generator or source 350 for generating a light signal to be directed onto an object such as, for example, the face of a human subject. The generated light is reflected from the face of the human subject and ins received onto an image sensor 340 wherein the image sensor 340 is configured to generate an electronic image signal representative of an image of the object. In one embodiment, the reflected light signal includes a first light signal from light reflected directly from the target surface of the object such as from the skin of a human subject and, in addition, includes a second light signal from light reflected and/or scattered and reflected from the dermis sub-surface of the skin of the human subject. In one embodiment, the light source 350 generates polarized light. In another embodiment, the light source 350 generates infrared light. In a further embodiment, the light source 350 generates visible light.

In one embodiment, the computer system 300 is configured to determine a depth measurement of the skin of the human subject. A time of flight of the first light signal from light reflected directly from the target surface of the object is determined. Also, a time of flight of the second light signal from light reflected and/or scattered and reflected from the dermis sub-surface of the skin of the human subject is determined by a correlation processor of the system. A difference in the time of flight of the first light signal from light reflected directly from the target surface of the object and of the second light signal from light reflected and/or scattered and reflected from the dermis sub-surface of the skin of the human subject is determined by the correlation processor. A depth measurement or thickness measurement of the facial skin of the human object is calculated by the correlation processor in accordance with the difference value and a speed of propagation parameter relative to the first and second light signals.

Computer system 300 also includes a communication interface 318 coupled to bus 302. Communication interface 318 provides a two-way data communication coupling computer system 300 to a communication link 320 that is employed for communicating with other devices belonging to a predefined group. Computer system 300 can send messages and receive data, including program codes, through a network via communication link 320, and communication interface 318.

Figure 4:
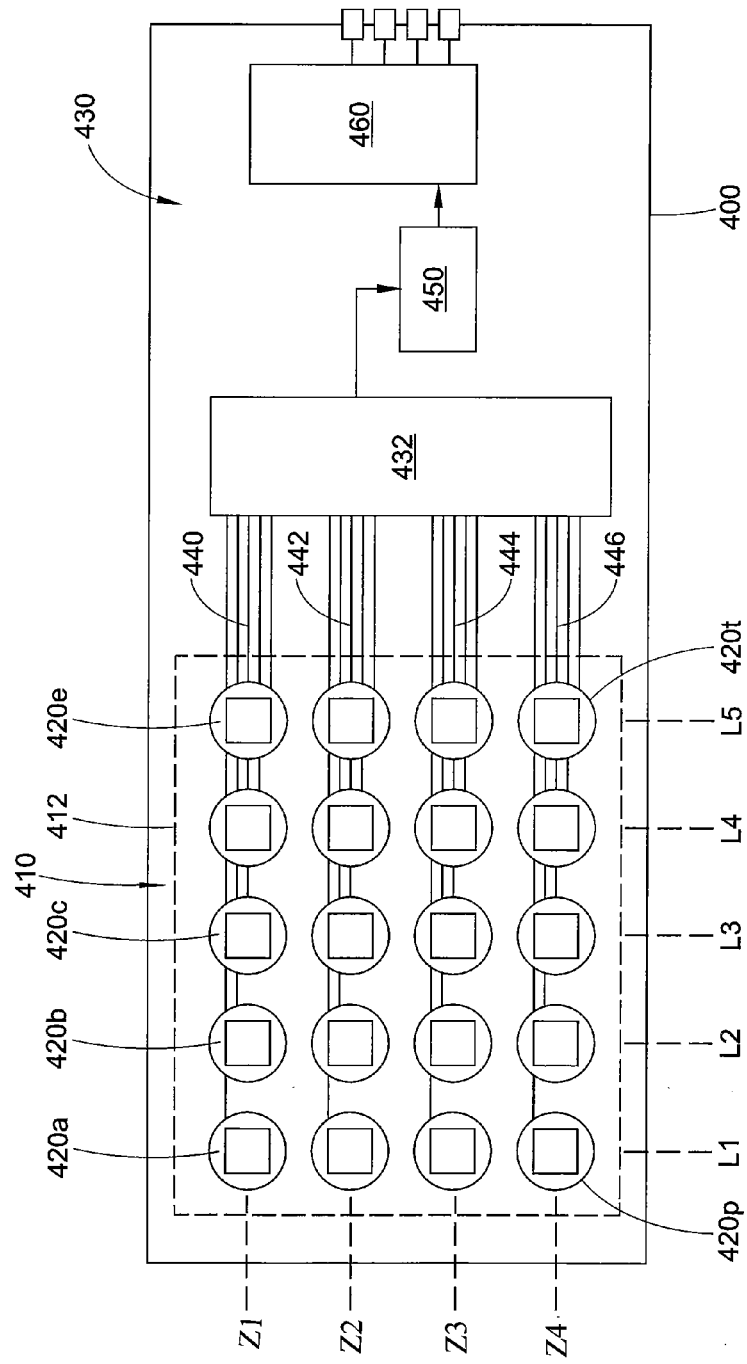
FIG. 4 is a schematic plan view of an opto-electronic image sensor used in the systems of FIGS. 1-3 in accordance with an example embodiment.

Turning now to FIG. 4, an image sensor 400 used in the system of FIGS. 1-3 is illustrated in accordance with an example embodiment. In this embodiment, the image sensor 400 includes a matrix 410 of camera systems 420a-420t formed on the image sensor 400 in an imaging area 412. As shown, the imaging area 412 includes twenty (20) camera systems arranged into four (4) rows Z1-Z4 and five (5) columns L1-L5. Each camera system 420a-420t of the example embodiment is a complete camera including a CMOS sensor array defining a focal plane generating pixel data, at least one lens for concentrating the image onto the focal plane, and at least one filter for filtering the image prior to being received by the CMOS sensor array. In an embodiment to be described in greater detail below, the focal planes of each camera of the CMOS sensor array are divided into two or more sub-focal planes, wherein each of the sub-focal planes is provided with a corresponding color micro-filter. In the example embodiment, the focal planes are divided into four (4) sub-focal planes wherein the focal plane lens of each camera of the CMOS sensor array is correspondingly divided into four (4) color micro-filters.

The image sensor 400 includes communication, control, and processing electronics 430 for interfacing the matrix 410 of camera systems 420a-420t with the computer system 300 (FIG. 3). The electronics 430 includes a frame assembler 432 operably connected with the plurality of camera systems 420a-420t by sets of data and control busses 440, 442, 444, and 446. The frame assembler 432 of the example embodiment is operable to receive analog signals from the matrix 410 of camera systems 420a-420t, store data representative of those signals at selected points in time, buffer the data, and deliver the buffered data as frames in accordance with selective control signals.

An output controller 450 is disposed between the frame assembler 432 and a buffer circuit 460 for controlling the operation of the frame assembler 432 to deliver the one or more frames of data representative of image data to the buffer circuit 460. In an embodiment, the frame assembler 432, output controller 450, and buffer circuit 460 are operable to generate sets of data representative of images at each camera system 420a-420t over time or at any one or more points in time as necessary or desired.

Figure 5:
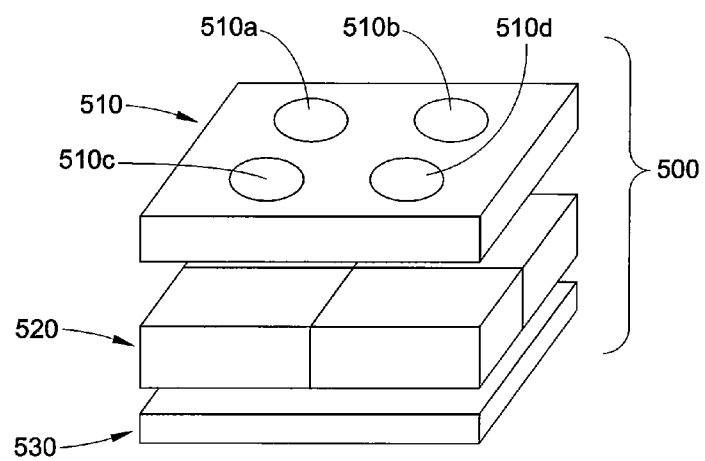
FIG. 5 is a schematic perspective view of a representative opto-electronic camera system forming the matrix of the image sensors of FIG. 4.

With reference next to FIG. 5, the general structure of a camera system 500 representative of the plural camera systems 420a-420t of FIG. 4 is illustrated. The representative camera 500 includes an imaging lens array 510, a color filter 520, and a detector array 530. The detector array 530 of the example embodiment may be the same as in a conventional camera and as such may include a 6 mega pixel array or any size pixel array as may be desired.

In general, in accordance with an embodiment, a camera 500 is provided for biometric mapping of a target object. The camera 500 includes an imaging lens array 510, a color filter array 520, a light detector array 530, and a processor 134 (FIG. 1) 304 (FIG. 3) operatively connected with the light detector array. The imaging lens array includes an n×m array of sub-camera imaging lenses. Each sub-camera imaging lens of the n×m array of sub-camera imaging lenses receives a reflected light signal reflected from the target object and focuses the reflected light signal to a focused reflected light signal. The color filter array includes an n×m array of sub-camera color filters. Each sub-camera color filter of the n×m array of sub-camera color filters receives a corresponding one of the focused reflected light signals and filters the focused reflected light signal to a color filtered focused reflected light signal. The light detector array includes an n×m array of sub-camera light detectors. Each sub-camera light detector of the n×m array of sub-camera light detectors receives a corresponding one of the color filtered focused reflected light signal and generates an output signal representative of an image of the target object. The processor 134 (FIG. 1) 304 (FIG. 3) is operatively connected with the light detector array. The processor processes the output signal representative of an image of the target object and generates a biometric mapping image signal representative of a condition of the target object.

In the example embodiment, the n×m array of sub-camera color filters of the camera includes a set of color filters configured to filter selected narrow bands of wavelengths of light optimized for imaging human skin as the target object. Although red-pink, pink-red, green-yellow, and yellow-green color filters are described herein, it is to be appreciated that the embodiments are not so limited and may comprise any one or more color filters or color filter arrays for filtering the reflected light signals in any selected narrow bands of wavelengths of light optimized for imaging human skin as the target object as necessary or desired.

In accordance with the sample embodiment, the camera system 500 is of a compound eye topology wherein the imaging lens array 510 includes a 2×2 array of lenses 510a-510d. Each of the lenses 510a-510d addresses a quarter of the area of the imaging plain defined by the detector array 530. Thus, in the compound eye topology of the example embodiment, the camera system 500 is formed as an aggregation of a set of sub-cameras, each of the sub-cameras being formed by a combination of a lens 510a-510d, a corresponding portion of the color filter 520, and a corresponding portion of the detector array 530.

In the embodiment shown in FIG. 5, there are four (4) sub-cameras forming the camera system 500 representative of each of the plural camera systems 420a-420t of FIG. 4. It is to be appreciated, however, that the imaging lens array of the camera system can be provided to have any size such as, for example, a 3×3 array, a 4×4 array, or any n×m array.

In accordance with an example embodiment, a method of constructing an imaging device of the type described for biometric mapping of a target object includes providing a light detector, disposing a color filter on the light detector, and disposing an imaging lens on the color filter. The disposing the imaging lens includes disposing an imaging lens array including an n×m array of sub-camera imaging lenses on the color filter. Each sub-camera imaging lens of the n×m array of sub-camera imaging lens is configured to receive a reflected light signal reflected from the target object and to focus the reflected light signal to a focused reflected light signal. The disposing the color filter includes disposing a color filter array including an n×m array of sub-camera color filters on the light detector. Each sub-camera color filter of the n×m array of sub-camera color filter is configured to receive a corresponding one of the focused reflected light signals and to filter the focused reflected light signal to a color filtered focused reflected light signal. The providing the light detector array includes providing a light detector array includes an n×m array of sub-camera light detectors. Each sub-camera light detector of the n×m array of sub-camera light detectors is configured to receive a corresponding one of the color filtered focused reflected light signal and to generate an output signal representative of an image of the target object.

Figure 6:
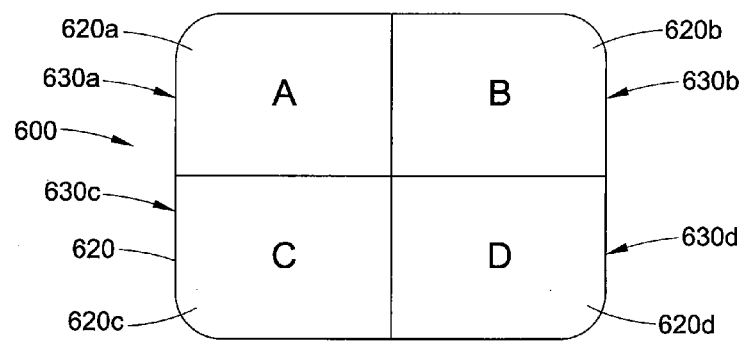
FIG. 6 is a plan view of a 2×2 color filter array according to an example embodiment.

FIG. 6 shows a plan view of a light filter 600 used in the example embodiment. In its preferred form, the filter 600 is a color light filter 620 representative of the color filter 520 used in the camera system 500 of FIG. 5. As shown, the color filter 620 is divided into an appropriate set of color sub-filters 620a-620d corresponding to respective regions 630a-630d of the filter 600, wherein each of the color sub-filters 620a-620d is disposed adjacent to a corresponding one of the lenses 510a-510d of the imaging lens array 510 (FIG. 5). The images from each of the sub-focal planes of the four sub-cameras are provided to the processor 304 (FIG. 3) where they are combined in accordance with logic stored in an memory and executed by the processor of the image acquisition system to form a composite color image. In the example embodiment, images from each of the four sub-cameras of each of the camera systems 420a-420t are provided to the processor 304 where they are combined to form a composite color image.

Figure 7A:
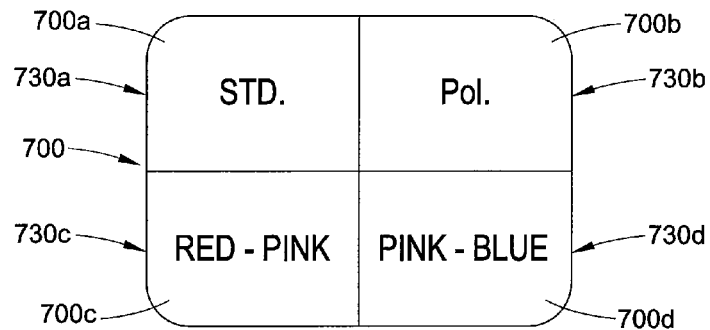
FIGS. 7a-7e are plan views of various 2×2 color filter arrays according to example embodiments.

FIGS. 7a-7e are plan views of various 2×2 color filter arrays 700-708 in accordance with example embodiments. With reference first to FIG. 7a, the color filter array 700 includes a standard filter 700a in the first region 730a, a polarizing filter 700b in the second region 730b, a red-pink filter 700c in the third region 730c, and a pink-blue filter 700d in the fourth region 730d.

Figure 7B:
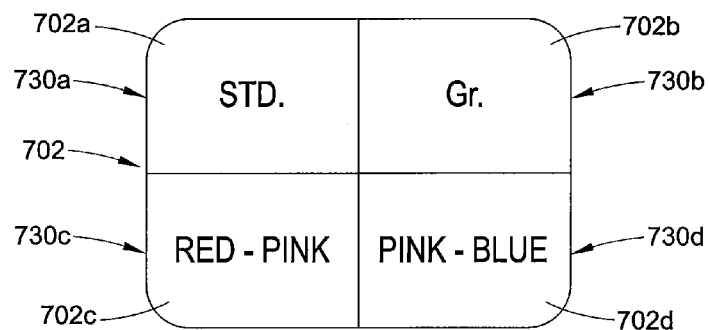

Another color filter 702 in accordance with a further example embodiment such as shown in FIG. 7b includes a standard filter 702a in the first region 730a, a grating filter 702b in the second filter region 730b, a red-pink filter 702c in the third region 730c, and a pink-blue filter 702d in the fourth region 730d.

Figure 7C:
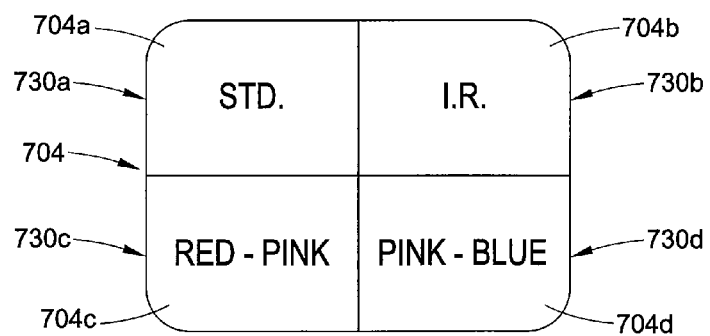

In yet another embodiment such as shown in FIG. 7c, a filter 704 includes a standard sub-filter 704a in a first region 730a, an infrared sub-filter 704b in a second region 730b, a red-pink sub-filter 704c in a third region 730c, and a pink-blue filter 704d in a fourth region 730d.

Figure 7D:
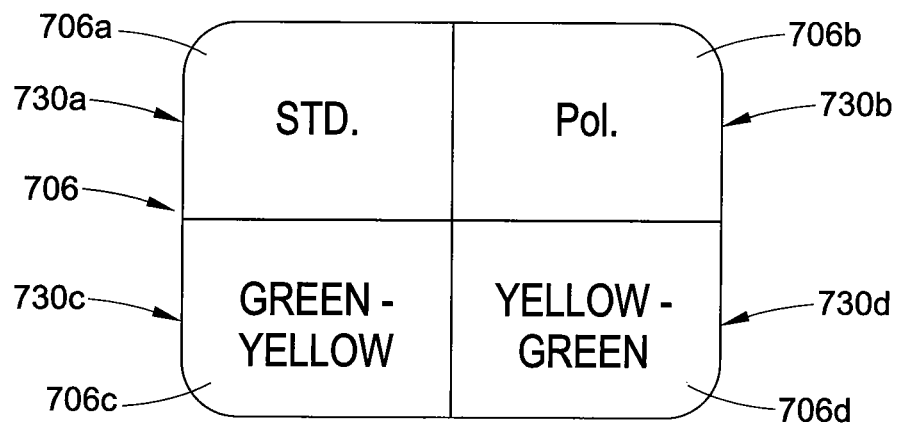
Figure 7E:
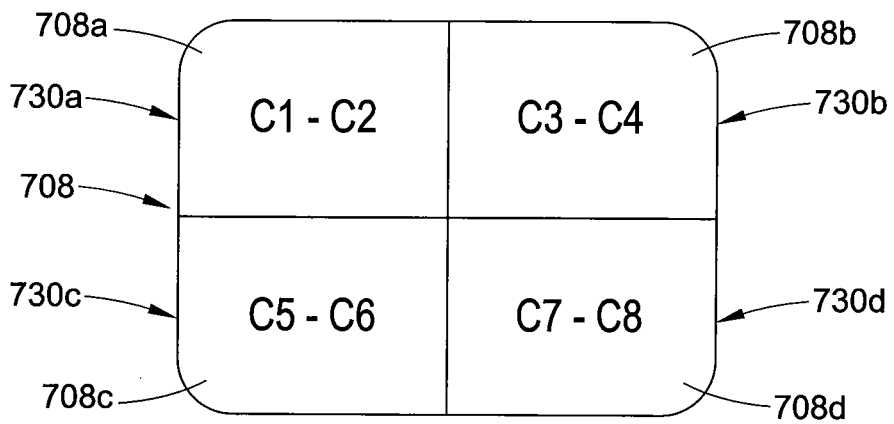

In yet a further example embodiment such as shown in FIG. 7d, a filter 706 includes a standard sub-filter 706a in a first region 730a, a polarizing sub-filter 706b in a second region 730b, a green-yellow sub-filter 706c in a third region 730c and a yellow-green sub-filter 706d in a fourth region 730d.

In accordance with yet a further example embodiment such as shown in FIG. 7b, a filter 708 includes a first sub-filter 708a in a first region 730a for filtering light between a first color C1 and a second color C2. A second sub-filter 708b is disposed in a second region 730b of the filter 708 for filtering light between a third color C3 and a fourth color C4. A third sub-filter 708c is disposed in a third region 730c for filtering light between a fifth color C5 and a sixth color C6. Lastly, a fourth sub-filter 708d is disposed in a forth region 730d for filtering light between a seventh color C7 and an eighth color C8. It is to be appreciated that although the sub-filters 708a-708d are indicated as filtering light between certain selective colors C1-C8, any of these selective colors and/or selected color zones can be overlapping as necessary or desired.

Figure 8B:
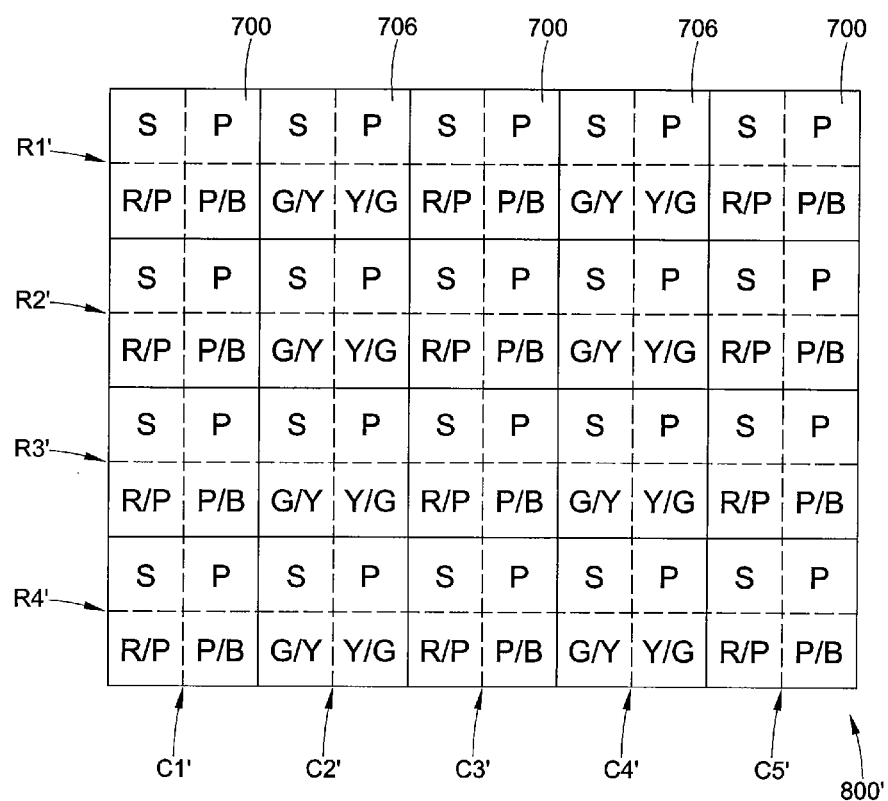

FIGS. 8a and 8b are plan views of composite color filter members 800, 800' in accordance with example embodiments. Each of the color filter members 800, 800' is formed of a collection of one or more of the filter arrays 700-708 as shown in FIGS. 7a-7e arranged into particular selected patterns as necessary or desired for targeting certain features of the imaged object. In the example embodiments, the color filter members 800, 800' are arranged into selected repeated patterns of alternating columns for each row of the filter member. However, other patterns or arrangements are possible in other embodiments.

As shown in FIG. 8a, each row R1-R4 of the color filter member 800 is formed as a repeating pattern of a first filter array 700 such as shown in FIG. 7a. That is, in the example embodiment illustrated, the color filter member 800 is comprised of a plurality of tiled filter arrays 700 having a construction of sub-filters 700a-700d substantially as shown in FIG. 7a including an arrangement of a standard sub-filter element 700a, a light polarizing sub-filter element 700b, a red to pink sub-filter element 700c, and a pink to blue sub-filter element 700d.

Similarly, as shown in FIG. 8b, each row R1'-R4' of the color filter member 800' is formed as an alternating pattern of a first filter array 700 such as shown in FIG. 7a, and of a second filter array 706 such as shown in FIG. 7d. In the example embodiment, the odd columns C1', C3', and C5' are comprised of the first filter arrays 700 such as shown in FIG. 7a and the even columns C2' and C4' are comprised of the second filter arrays 706 such as shown in FIG. 7d wherein the first filter arrays 700 include an arrangement of a standard sub-filter element 700a, a light polarizing sub-filter element 700b, a red to pink sub-filter element 700c, and a pink to blue sub-filter element 700d, and further wherein the second arrays 706 include an arrangement of a standard sub-filter element 706a, a light polarizing sub-filter element 706b, a green to yellow sub-filter element 706c, and a yellow to green sub-filter element 706d.

In the example embodiments, each of the color filter member 800, 800' are configured to be disposed within the imaging area 412 (FIG. 4) so that the intersection of each of the columns and rows of the color filter members are arranged to be adjacent to each of one of the camera systems 420a-420t of the illustrated image sensor 400. In their preferred form, the color filter members 800, 800' comprise micro-optic lenses formed separately from the wafers forming the underlying camera systems or sub-systems and are located or disposed on top of or immediately adjacent to the camera systems or sub-systems.

In the example embodiments, the color filter member 800 is particularly well suited for imaging the face of a human to collect filtered image data usable for assessing potential diseases or pre-disease conditions related to blood diseases, circulatory problems, or the like. Also, the color filter member 800' of the example embodiment is particularly well suited for imaging the face of a human to collect filtered image data useful for assessing potential disease or pre-disease conditions related to eczema, skin rashes, jaundice, liver disease, or the like.

The color filter members 800, 800' of the example embodiments are inherently trained or well-suited for certain particular sets or ranges of color information from the subject 10 (FIG. 1). For example, the color filter member 800 comprises an array of color filter layers tuned to detect wavelengths close to the color red. The color filter member 800' comprises an array of color filter layers tuned to detect wavelengths close to the color red as well as wavelengths close to the colors green and yellow. In other embodiments, the color filter members may comprise arrays of one or more color filter layers tuned to detect wavelengths close to any selected one or more visible or invisible (to humans) wavelengths as necessary or desired in order to obtain the desired imaging data.

Figure 9:
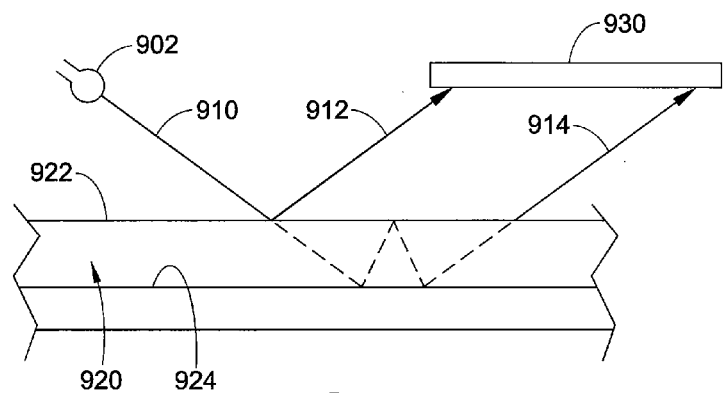
FIG. 9 is a schematic view of polarized light from a polarized light source reflected from skin in accordance with an embodiment.

For example, the infrared sub-filter 704b of the filter array 704 is useful to collect data representative of features of the imaged target which are invisible to the human eye. Also, combinations of the polarizing sub-filter 700b of the filter array 700, and the grating sub-filter 700b of the filter array 702, are useful in combination with a polarized light source 120, 350 for example, to collect sub-dermal data for analysis. As shown in FIG. 9 for example, polarized signal light 910 from a source 902, for example any of light sources 120 (FIG. 1), 260 (FIG. 2), or 350 (FIG. 3) is directed to a target surface 922 such as facial skin 920, wherein a portion of the polarized light 910 is reflected from the target surface 920 as reflected polarized light 912, and another portion of the polarized light 910 penetrates the target surface 922 and is reflected from the dermis sub-surface 924 of the facial skin as reflected sub-surface scattered light 914. Both the reflected polarized light 912 as well as the reflected sub-surface scatter light 914 are collected on a camera system 930. In the example embodiment, the camera system 930 comprises a camera having a construction such as the camera system 500 (FIG. 5) and includes a filter 600 (FIG. 6) comprising any one or more of the filter arrays 700-708 (FIGS. 7a-7e) or any other one or more filter arrays as necessary or desired.

Each of the reflected surface light signal 921 and the reflected and/or scattered and reflected sub-surface light signal 914 are rich in disease detection and analysis information. This disease detection and analysis information is collected as color map data by an image sensor in accordance with the example embodiments.

Further in accordance with the example embodiments, biometric mapping of facial or a patch or patches of skin color is performed using computational imaging apparatus and methods as described herein for preventative health care and for fast diagnosis of diseases and/or of the early onset of disease. The embodiments herein utilize one or more CMOS cameras in combination with one or more color filter arrays and suitable logic executed by one or more processors of an image acquisition system to develop gradient color maps of the facial skin to algorithmically predict early development of various diseases such as inflammation, musco-skelatal ailments and others.

Figure 10:
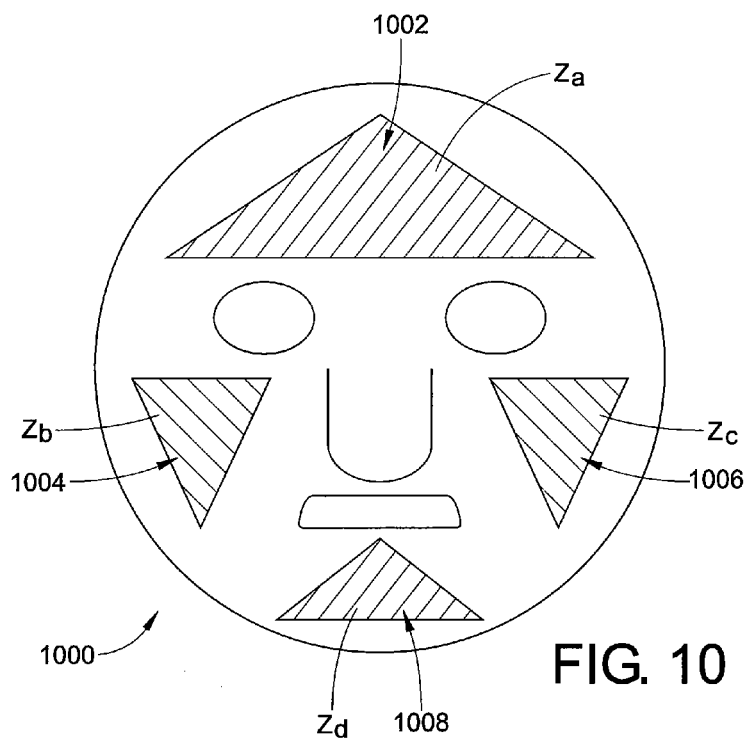
FIG. 10 is a schematic view of an image of a human face divided into selected imaging zones in accordance with an example embodiment.

In accordance with the example embodiments of the methods and systems described herein directed to the imaging of human anatomy, as illustrated in FIG. 10, the face 1000 of a human subject is divided into a plurality of imaging zones including a top zone 1002, a left zone 1004, a right zone 1006, and a bottom zone 1008. The zones may comprise the top, left, right, and bottom portions, regions or areas of any arbitrary subject of imaging and may take on any form such as, for example, circular zones, rectangular zones, triangular zones, or zones having any regular, irregular, or combinations of regular and irregular patterns. In accordance with the example embodiments, however, for a target imaging subject comprising a human face 1000, the upper zone 1002 is selected as a triangular forehead zone $Z_a$. The left and right zones 1004, 1006 in the example embodiment are triangular left and right cheek zones $Z_b$ and $Z_c$, respectively. Lastly, the lower imaging zone 1008 is, in the example embodiment, a facial zone comprising a triangular chin imaging area $Z_d$.

In accordance with the embodiments described herein, the imaging zones 1002-1008 are not limited to spacially separated imaging zones but, rather, may overlap for enhanced imaging and analysis of the target area as necessary or desired. In addition, it is to be appreciated that each of the imaging zones 1002-1008 can be selectively imaged using one or more color pallets wherein separate color pallets can be used for imaging each of the regions 1002-1008 separately, or in various combinations.

Figure 11A:
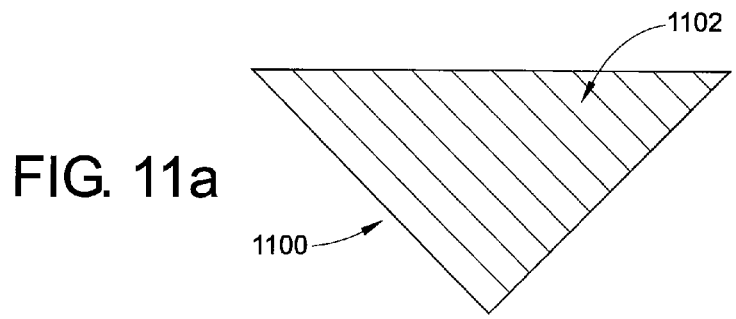
FIGS. 11a-11c are schematic views of a color tuning scheme using overlapping imaging regions in accordance with an example embodiment.
Figure 11B:
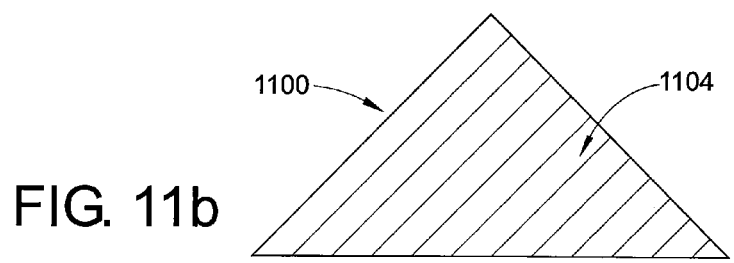
Figure 11C:
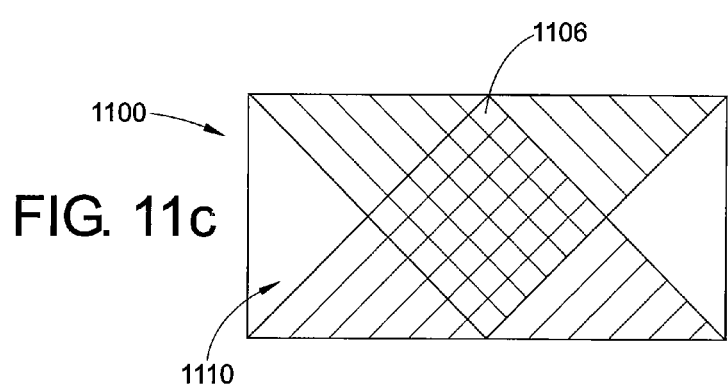

FIGS. 11a-11c illustrate a color tuning scheme 1100 for specific colors using triangulation for intensity calculations. A first imaging area 1102 is imaged using a first filter array such as, for example, one or more of the filter arrays 700-708 (FIG. 7). A second imaging area 1104 shown in FIG. 11b is imaged using a second filter array such as, for example, one or more of the filter arrays 700-708. In accordance with an example embodiment, the first imaging area 1102 is made to overlap the second imaging area 1104 in an overlap imaging area 1106 such as, for example, shown in FIG. 11c. In the embodiment, a matrix of weight values ranging from 1 to 256 are assigned to the imaging results in the box area 1110 shown in FIG. 11c. Weights in the overlap area 1106 are weighted with one or more of the color filter arrays 700-708 as necessary or desired.

Figure 12:
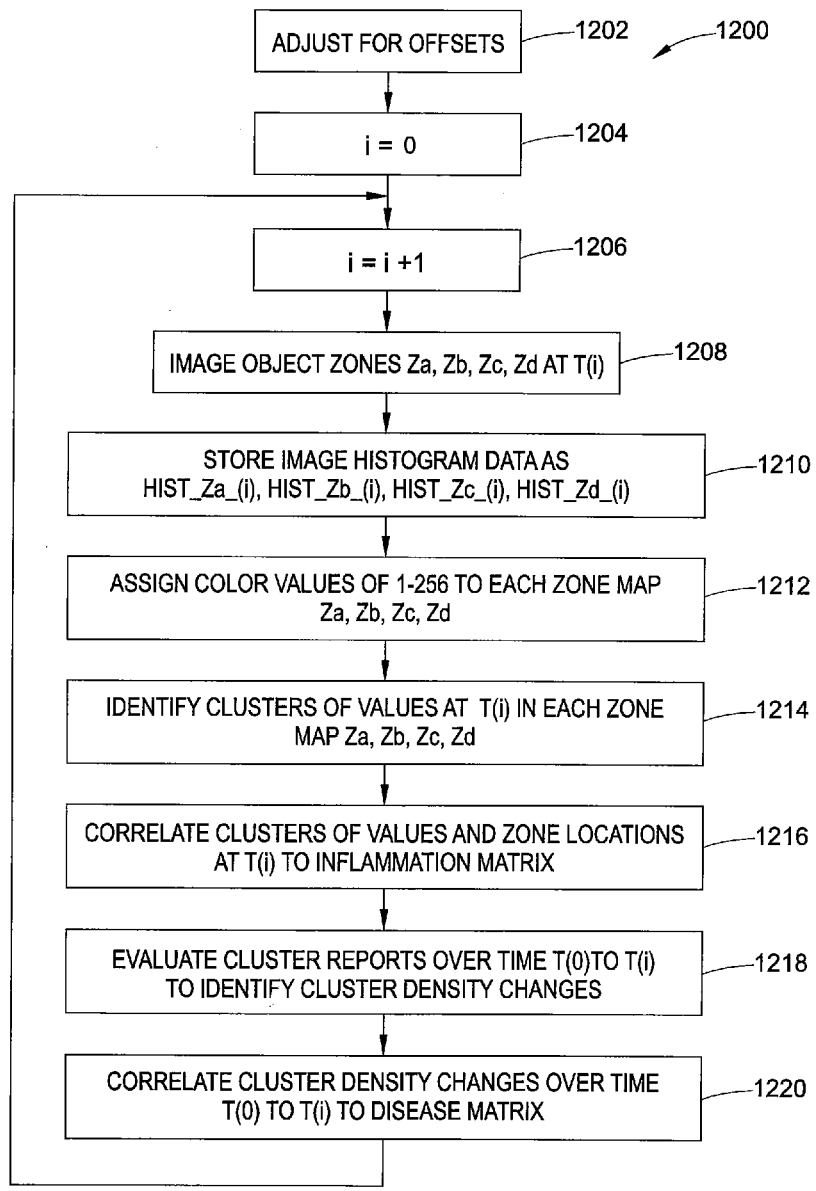
FIG. 12 is a flow chart of a method of biometric mapping of facial skin in accordance with an example embodiment.

Turning now to FIG. 12, a flow chart is illustrated of a method 1200 of biometric mapping of the facial skin in accordance with an example embodiment. As shown there, at an initial step 1202, the image acquisition system 100 (FIG. 1) executes an initialization procedure for establishing one or more offset values in order to compensate for minor disparities between the electronic components of the system such as, for example, of variations in the camera systems 420a-420t (FIG. 4). In accordance with an example, a closed shutter picture is taken for establishing absolute current values and distribution of current values for each of the elements within the matrix 410. In an example, the absolute currents and distributions of currents are first determined for odd focal planes L1, L3, L5 for each of the rows Z1-Z4, followed by absolute current and distribution current measurements for the even focal planes L2 and L4 for each of the rows Z1-Z4. Thereafter, an open aperture picture of a target area such as, for example, on the face of this subject is taken and, thereafter, the absolute current values and distribution of current values for the even and odd focal planes are subtracted from the open aperture picture of the target area in order to establish offsets as necessary or desired. A further initialization step 1204 sets a counter value i to a predetermined initialization value of zero.

At step 1206, the counter value is incremented and, at step 1208, the associated object 1000 (FIG. 10) is imaged, and in particular, each of the upper, left, right, and lower zones 1002-1008 of the human object are imaged wherein data representative of a triangular forehead zone $Z_a$ a triangular left cheek zone $Z_b$ a triangular right cheek zone $Z_c$ and a triangular chin zone $Z_d$ is obtained at an initialization time $T_i$.

The data for each of the image zones $Z_a$-$Z_d$ is stored as histogram data at step 1210.

Color values for each of the zone maps $Z_a$-$Z_d$ are assigned as step 1212. In the example embodiment, the color values are stored as 8 bit values and, accordingly, have a range from 0-156.

At step 1214, cluster of values are identified at the initial time $T_i$ in each zone map $Z_a$-$Z_d$.

The clusters are correlated in terms of the values of the clusters and the zone locations of the clusters with an inflammation matrix at step 1216. In accordance with the example embodiment, the inflammation matrix may be stored locally such as, for example, in the memory 136 (FIG. 1) or in the main memory 303 (FIG. 3) or remotely such as, for example, in the memory 146 of the second set of remote computational devices 140 connected with the imaging device by means of a suitable network 142.

At step 1218, a series of cluster reports are evaluated over time for multiple images of the object zones $Z_a$-$Z_d$ to identify density changes over time.

At step 1220, the cluster density changes over time are correlated with a disease matrix which may be stored locally or remotely as identified above.

The embodiments herein have been described with reference to preferred structures and method steps. However, it is to be appreciated that the claims herein are not limited to those precise structures, steps, or their specific descriptions. Rather, the claims are to be given their broadest possible interpretation as appropriate.

In addition, while certain embodiments have been described, these embodiments have been presented by way of example only, and are not intended to limit the scope of the claimed inventions. Indeed, the novel embodiments described herein may be embodied in a variety of other forms; furthermore, various omissions, substitutions and changes in the form of the embodiments described herein may be made without departing from the spirit of the claimed inventions. The accompanying claims and their equivalents are intended to cover such forms or modifications as would fall within the scope and spirit of the inventions.

The invention claimed is:

1. A diagnostic system comprising:
a light filter operable to filter light reflected from an associated object to produce a filtered light signal; a light sensor configured to receive the filtered light signal and to generate a first electronic image signal representative of an image of the object in accordance with the filtered light signal; a non-transient memory storing a first electronic diagnostic signal representative of a predetermined malady associated with the object;
a correlation processor operable to determine a correlation between the first electronic image signal and the first electronic diagnostic signal, and to generate a correlation signal representative of a strength of the correlation;
an assessment processor operable to determine a diagnosis of the associated object based on the correlation signal, and to generate a diagnosis signal in accordance with the diagnosis; wherein
the light sensor is configured to receive a first set of filtered light signals and to generate a first set of electronic image signals representative of images of the object during a first time period; the correlation processor is operable to determine a change trend in one of the first set of electronic image signals, and to generate a trend correlation signal representative of a strength of the change trend; and
the assessment processor is operable to determine the diagnosis of the associated object based on the trend correlation signal, and to generate the diagnosis signal in accordance with the diagnosis.

2. The diagnostic system according to claim 1, wherein:
the light sensor comprises a CMOS sensor array generating an array of image pixel data;
the light filter is disposed on the CMOS sensor array; and,
the light filter comprises at least one of a red to pink sub-filter, a pink to blue sub-filter, a yellow to green sub-filter, a green to yellow sub-filter, or combinations of one or more of red to pink sub-filters, pink to blue sub-filters, yellow to green sub-filters, and green to yellow sub-filters.

3. The diagnostic system according to claim 2, wherein:
the light filter comprises at least one of a depolarization sub-filter, a grating element sub-filter, or combinations of one or more of depolarization sub-filters and grating element sub-filters.

4. The diagnostic system according to claim 3, wherein:
the light filter comprises an array of light sub-filters, wherein each light sub-filter of the array of light sub-filters is disposed adjacent to a light sensor of the CMOS sensor array.

5. The diagnostic system according to claim 1, further comprising:
an input in selective communication with an associated network, the input being operable to receive the first electronic diagnostic signal from an associated source via the associated network.

6. The diagnostic system according to claim 1, further comprising:
an output operable to generate a diagnosis result signal in accordance with the diagnosis signal.

7. The diagnostic system according to claim 1 wherein the malady is associated with a skin condition of a human subject.

8. The diagnostic system of claim 1 wherein the malady is associated with a disease condition of a human subject.

9. A method of biometric mapping of facial skin, the method comprising: filtering, by a light filter, light reflected from an associated object to produce a filtered light signal; receiving the filtered light signal by a light sensor and generating a first electronic image signal representative of an image of the object in accordance with the filtered light signal;
storing in a non-transient memory a first electronic diagnostic signal representative of a predetermined malady associated with the object;
determining by a correlation processor a correlation between the first electronic image signal and the first electronic diagnostic signal, and generating a correlation signal representative of a strength of the correlation;
determining by an assessment processor a diagnosis of the associated object based on the correlation signal, and generating a diagnosis signal in accordance with the diagnosis; generating by an output a diagnosis result signal in accordance with the diagnosis signal;
filtering, by the light filter, a first light signal from light reflected directly from a target surface of the facial skin and a second light signal from light reflected from a target dermis sub-surface of the facial skin; determining by the correlation processor a time of flight of the first light signal from light reflected directly from the target surface of the facial skin; determining by the correlation processor a time of flight of the second light signal from light reflected from the target dermis sub-surface of the facial skin;
determining by the correlation processor a difference value in the time of flight of the first light signal from light reflected directly from the target surface of the facial skin and of the second light signal from light reflected from the target dermis sub-surface of the facial skin; and determining by the correlation processor a depth measurement of the facial skin of the human object in accordance with the difference value and a speed of propagation parameter stored in the non-transient memory relative to the first and second light signals.

10. The method according to claim 9, wherein:
the receiving the filtered light signal by the light sensor comprises receiving the filtered light signal by a CMOS sensor array generating an array of image pixel data;
the filtering comprises filtering by a light filter disposed on the CMOS sensor array, wherein the light filter comprises at least one of a red to pink sub-filter, a pink to blue sub-filter, a yellow to green sub-filter, a green to yellow sub-filter, or combinations of one or more of red to pink sub-filters, pink to blue sub-filters, yellow to green sub-filters, and green to yellow sub-filters.

11. The method according to claim 10, wherein:
   the filtering comprises filtering by a light filter comprising at least one of a depolarization sub-filter, a grating element sub-filter, or combinations of one or more of depolarization sub-filters and grating element sub-filters.

12. A camera for biometric mapping of a target object, the camera comprising: an imaging lens array comprising an n×m array of sub-camera imaging lenses, wherein n and m are positive integers greater than or equal to one, each sub-camera imaging lens of the n×m array of sub-camera imaging lenses receiving a reflected light signal reflected from the target object and focusing the reflected light signal to produce a focused reflected light signal;
   a color filter array comprising an n×m array of sub-camera color filters, each sub-camera color filter of the n×m array of sub-camera color filters receiving a corresponding one of the focused reflected light signals and filtering the focused reflected light signal to produce a color filtered focused reflected light signal; and,
   a light detector array comprising an n×m array of sub-camera light detectors, each sub-camera light detector of the n×m array of sub-camera light detectors receiving a corresponding one of the color filtered focused reflected light signal and generating an output signal representative of an image of the target object; and,
   a processor operatively connected with the light detector array, the processor processing one or more of the output signal representative of an image of the target object, determining a change trend in at least one of the output signals, generating a trend correlation signal representative of a strength of the change trend, determining a malady associated with the target object based at least in part on the trend correlation signal, and generating a biometric mapping image signal representative of the malady associated with the target object.

13. The camera according to claim 12, wherein:
   the n×m array of sub-camera color filters comprises a set of color filters configured to filter selected narrow bands of wavelengths of light optimized for imaging human skin as the target object.

14. The camera according to claim 12, wherein the n×m array of sub-camera color filters comprises;
   at least one polarizing filter;
   at least one red-pink light filter; and,
   at least one pink-blue light filter.

15. The camera according to claim 12, wherein the n×m array of sub-camera color filters comprises;
   at least one grating filter;
   at least one red-pink light filter; and,
   at least one pink-blue light filter.

16. The camera according to claim 12, wherein the n×m array of sub-camera color filters comprises;
   at least one infrared light filter;
   at least one red-pink light filter; and,
   at least one pink-blue light filter.

17. The camera according to claim 12, wherein the n×m array of sub-camera color filters comprises;
   at least one polarizing filter;
   at least one green-yellow light filter; and,
   at least one yellow-green light filter.

18. A method of constructing an imaging device for biometric mapping of a target object, the method comprising: providing a light detector; providing a processor operatively connected with the light detector; disposing a color filter on the light detector; and, disposing an imaging lens on the color filter; wherein the disposing the imaging lens comprises disposing an imaging lens array including an n×m array of sub-camera imaging lenses on the color filter, wherein n and m are positive integers greater than or equal to one, each sub-camera imaging lens of the n×m array of sub-camera imaging lens being configured to receive a reflected light signal reflected from the target object and to focus the reflected light signal to produce a focused reflected light signal; wherein the disposing the color filter comprises disposing a color filter array including an n×m array of sub-camera color filters on the light detector, each sub-camera color filter of the n×m array of sub-camera color filter being configured to receive a corresponding one of the focused reflected light signals and to filter the focused reflected light signal to produce a color filtered focused reflected light signal;
   wherein the providing the light detector array comprises providing a light detector array includes an n×m array of sub-camera light detectors, each sub-camera light detector of the n×m array of sub-camera light detectors being configured to receive a corresponding one of the color filtered focused reflected light signal and to generate an output signal representative of an image of the target object;
   wherein the processor is configured to receive one or more of the output signals representative of an image of the target object from the light detector, determine a change trend in at least one of the output signals, generate a trend correlation signal representative of a strength of the change trend, determine a malady associated with the target object based at least in part on the trend correlation signal, and generate a biometric mapping image signal representative of the malady associated with the target object.

19. The method of constructing an imaging device for biometric mapping of a target object according to claim 18, wherein:
   the disposing the color filter on the light detector comprises disposing a color filter comprising at least one polarizing filter, at least one red-pink light filter, and at least one pink-blue light filter on the light detector.

20. The method of constructing an imaging device for biometric mapping of a target object according to claim 18, wherein:
   the disposing the color filter on the light detector comprises disposing a color filter comprising at least one infrared light filter, at least one red-pink light filter, and at least one pink-blue light filter on the light detector.

21. The method of constructing an imaging device for biometric mapping of a target object according to claim 18, wherein:
   the disposing the color filter on the light detector comprises disposing a color filter comprising at least one polarizing filter, at least one green-yellow light filter, and at least one yellow-green light filter on the light detector.

* * * * *